United States Patent
Bush et al.

(10) Patent No.: US 9,744,549 B2
(45) Date of Patent: Aug. 29, 2017

(54) SYSTEM AND METHOD FOR DISPENSING MATERIAL

(71) Applicant: The Procter & Gamble Company, Cincinnati, OH (US)

(72) Inventors: Stephan Gary Bush, Liberty Township, OH (US); Faiz Feisal Sherman, Mason, OH (US); Dana Paul Gruenbacher, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 214 days.

(21) Appl. No.: 14/658,280

(22) Filed: Mar. 16, 2015

(65) Prior Publication Data

US 2016/0271639 A1  Sep. 22, 2016

(51) Int. Cl.
    *B05B 17/04* (2006.01)
    *B05B 17/06* (2006.01)
    *A61L 9/03* (2006.01)
    *A61L 9/14* (2006.01)

(52) U.S. Cl.
    CPC ............ *B05B 17/0615* (2013.01); *A61L 9/03* (2013.01); *A61L 9/14* (2013.01); *B05B 17/0669* (2013.01); *A61L 2209/11* (2013.01); *A61L 2209/132* (2013.01)

(58) Field of Classification Search
    CPC ... B05B 17/0615; B05B 17/0669; A61L 9/03; A61L 9/14; A61L 2209/11; A61L 2209/132
    USPC ........ 239/4, 102.1, 102.2, 548, 552; 347/47, 347/68, 75
    See application file for complete search history.

(56) References Cited

U.S. PATENT DOCUMENTS

| | | | |
|---|---|---|---|
| 5,874,974 A | 2/1999 | Courian et al. | |
| 8,727,234 B2 | 5/2014 | Haran | |
| 8,821,802 B2 | 9/2014 | Haran | |
| 2002/0050533 A1* | 5/2002 | Hirota | B05B 17/0607 239/102.2 |
| 2002/0063752 A1 | 5/2002 | Clark | |
| 2006/0152550 A1* | 7/2006 | Tomita | B41J 2/14056 347/47 |
| 2009/0096839 A1 | 4/2009 | Olbrich et al. | |

(Continued)

FOREIGN PATENT DOCUMENTS

| | | |
|---|---|---|
| EP | 1510228 A1 | 3/2005 |
| EP | 1894727 A2 | 3/2008 |

OTHER PUBLICATIONS

International Search Report and Written Opinion dated May 4, 2016, 12 pages.

*Primary Examiner* — Steven J Ganey
(74) *Attorney, Agent, or Firm* — David K Mattheis

(57) ABSTRACT

A liquid dispensing method including steps of: providing a dispensing device having a refill time (RT) and repeatedly energizing the activation elements at a frequency greater than about 1/(RT). The device includes: a plurality of liquid dispensing elements, each element including: a chamber having a height (H), a nozzle having a diameter (D), an activation element having a length (L), and the refill time (RT); a liquid containing reservoir in fluid communication with the liquid dispensing elements; and a control element in electrical communication with the liquid dispensing elements. The ratio of the nozzle diameter (D) to chamber height (H) is between about 3 and about 10.

9 Claims, 2 Drawing Sheets

(56) References Cited

U.S. PATENT DOCUMENTS

Figure 1:
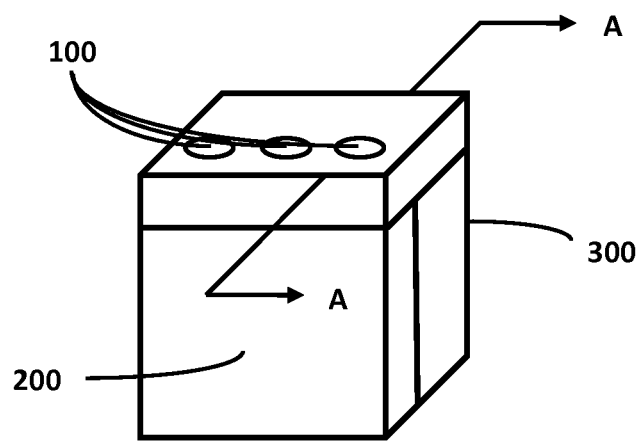
Figure 2:
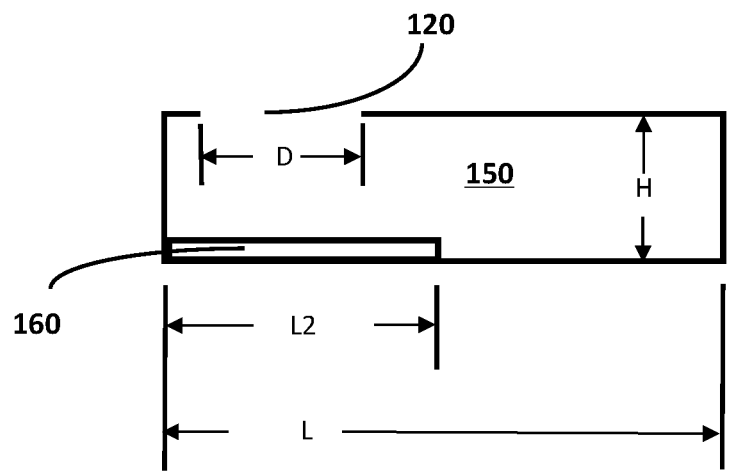

2009/0126722 A1 5/2009 Sugita et al.
2013/0010035 A1* 1/2013 Norikane ............. B41J 2/14233
239/102.2

* cited by examiner

SYSTEM AND METHOD FOR DISPENSING MATERIAL

FIELD OF THE INVENTION

The invention relates to systems and method for dispensing materials. The invention relates particularly to systems and method for dispensing materials by using a thermal jetting system.

BACKGROUND OF THE INVENTION

Dispensing materials via the heating of a volatile carrier to form a transport jet is well known. Thermal ink-jet systems provide a means for the creation and precise deposition of ink droplets upon a substrate. Thermal driven systems may also be used to drive the dispensing or dispersion of other materials, again by volatilizing a carrier or the actual material to be dispensed.

The 'atomization' of volatile oils to disperse them in an environment for the purpose of spreading a fragrance in the environment is also known. Typical dispersion systems create a set of oil droplets which disperse in the environment. Many such oil droplets rapidly settle out of the atmosphere of the environment resulting in an oily deposit upon surfaces, and more significantly, a reduction in the concentration of the fragrance oils in the environment's atmosphere.

What is needed is an improved system and method for the dispersion of materials into an environment such that the material may be easily dispersed in the environment and may also remain airborne for a longer period of time.

SUMMARY OF THE INVENTION

In one aspect, a liquid dispensing method includes steps of: providing a dispensing device having a refill time (RT) and repeatedly energizing the activation elements at a frequency greater than about 1/(RT). The device includes: a plurality of liquid dispensing elements, each element including: a chamber having a height (H), a nozzle having a diameter (D), an activation element having a length (L), and the refill time (RT); a liquid containing reservoir in fluid communication with the liquid dispensing elements; and a control element in electrical communication with the liquid dispensing elements. The ratio of the nozzle diameter (D) to chamber height (H) is between about 3 and about 10.

BRIEF DESCRIPTION OF THE DRAWINGS

FIG. 1 provides a schematic representation of an embodiment of the invention.

FIG. 2 provides a schematic sectional representation of a chamber of an embodiment of the invention, taken along section line AA of FIG. 1.

DETAILED DESCRIPTION OF THE INVENTION

The present disclosure is directed to a fluid delivery system configured to eject a working fluid from a thermal micro-fluidic die. The die includes one or more heating elements formed in a substrate. The substrate may be covered by a dielectric layer, shielding the heating elements from direct contact with the working fluid intended for ejection by the system. Each heating element is disposed adjacent to a fluid chamber and in turn to a nozzle disposed adjacent to the fluid chamber. Well known structures associated with electronic components and the details of semiconductor fabrication have not been included in the description.

In one aspect, the invention comprises an apparatus for dispensing a liquid into an environment. The apparatus comprises a reservoir containing the liquid. The reservoir is in fluid communication with a dispensing element or print head. The connection between the reservoir and the dispensing element enables the fluid to flow from the reservoir to flow into chambers of the dispensing element. The chambers are generally a rectangular prism and have a height (H), length (L) and width (W). One surface of the chamber includes an activation element of length L2. Each chamber is disposed adjacent to an orifice, or nozzle, which in turn is open to the external environment of the apparatus. In one embodiment, the ratio of the nozzle diameter D to the chamber height H is between about 3 and about 10. The ratio of the length L2 of the activation element to the chamber height H may be between about 3 and about 11.

Selective manipulation of the ratio of the length L2 to the chamber height H, and/or the ratio of the diameter D to the chamber height H in the design and fabrication of the chamber, die and nozzle elements may advantageously enable operating conditions for the system. Such conditions include the ability to discharge fluid from the nozzles at rates in excess of the ability of the fluid to completely refill the chambers. A consequence of this mode of operation is that the droplets of fluid discharged from the nozzles may be smaller than the nozzle diameter D, which may be an operational advantage when small drops are desired but small nozzle diameter is undesired or impractical.

A control element is disposed in electrical communication with the activation elements and enables the application of energy to the liquid by the activation elements.

Liquid disposed within the chamber may be selectively volatilized by the transfer of energy from the activation element to the liquid. The activation element may comprise a resistive heating element or a piezoelectric element. Upon the transfer of sufficient energy to the liquid, (for example in the case of thermal activation) at least a portion of the liquid will become superheated and will vaporize. The liquid within the chamber will be ejected via the nozzle into the external environment as one or more droplets.

In one embodiment, the frequency at which the activation element imparts energy pulses to the liquid within the chamber exceeds the frequency with which the liquid can physically refill the chamber. The activation element fires and activates the liquid before the chamber is completely filled by the liquid. In one embodiment, the activation elements may be fired at a frequency of greater than 5000 Hz for chambers having dimensions D~30 um, H~10 um, and L~50 um, with a fluid having surface tension of about 30 mN/m and viscosity of about 7 mPa·s.

As illustrated in FIG. 1, the device 1000, comprises a plurality of dispensing elements 100, a fluid reservoir 300 in communication with the dispensing elements, and a control element 200 in electrical communication with the dispensing elements.

FIG. 2 provides a sectional view of a portion of FIG. 1 taken along line AA, showing the interior structure of a dispensing element 100 having a chamber 150, a nozzle, 120 and an activation element 160.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liquid dispensing method, the method comprising steps of:
    providing a dispensing device, the device comprising:
        a plurality of liquid dispensing elements, each element comprising a chamber having a height (H), a nozzle having a diameter (D), an activation element having a length (L2), and a refill time (RT)
        a liquid containing reservoir in fluid communication with the liquid dispensing elements;
        a control element in electrical communication with the liquid dispensing elements;
    wherein the ratio of the nozzle diameter (D) to chamber height (H) is between about 3 and about 10; and
        repeatedly energizing the activation elements at a frequency greater than about 1/(RT).

2. The method according to claim 1 wherein the ratio of the activation element length (L2) to the chamber height (H) is between about 3 and about 11.

3. A liquid dispensing method, the method comprising steps of:
    providing a dispensing device, the device comprising:
        a plurality of liquid dispensing elements, each element comprising a chamber having a height (H) and a refill time (RT), a nozzle having a diameter (D), and an activation element having a length (L2),
        a liquid containing reservoir in fluid communication with the liquid dispensing elements;
        a control element in electrical communication with the liquid dispensing elements;
    wherein the ratio of the activation element length (L2) to the chamber height (H) is between about 3 and about 11; and
        repeatedly energizing the activation elements at a frequency greater than about 1/(RT).

4. A liquid dispensing device, the device comprising:
    a plurality of liquid dispensing elements, each element comprising a chamber having a height (H) and a refill time (RT), a nozzle having a diameter (D), and an activation element having a length (L2),
    a liquid containing reservoir in fluid communication with the liquid dispensing elements;
    a control element in electrical communication with the liquid dispensing elements;
wherein the ratio of the activation element length (L2) to the chamber height (H) is between about 3 and about 11.

5. The device according to claim 4 wherein the ratio of the nozzle diameter (D) to chamber height (H) is between about 3 and about 10.

6. Method of creating jetted drop size diameter<D by providing a dispensing device, the device comprising:
    a plurality of liquid dispensing elements, each element comprising a chamber having a height (H), a nozzle having a diameter (D), an activation element having a length (L2), and a refill time (RT)
    a liquid containing reservoir in fluid communication with the liquid dispensing elements;
    a control element in electrical communication with the liquid dispensing elements;
wherein the ratio of the nozzle diameter (D) to chamber height (H) is between about 3 and about 10; and
    repeatedly energizing the activation elements at a frequency greater than about 1/(RT).

7. The method according to claim 6 wherein the ratio of the activation element length (L2) to the chamber height (H) is between about 3 and about 11.

8. Method of creating jetted drop size diameter<D by providing a dispensing device, the device comprising:
    a plurality of liquid dispensing elements, each element comprising a chamber having a height (H) and a refill time (RT), a nozzle having a diameter (D), and an activation element having a length (L2),
    a liquid containing reservoir in fluid communication with the liquid dispensing elements;
    a control element in electrical communication with the liquid dispensing elements;
wherein the ratio of the activation element length (L2) to the chamber height (H) is between about 3 and about 11; and
    repeatedly energizing the activation elements at a frequency greater than about 1/(RT).

9. The device according to claim 8 wherein the ratio of the nozzle diameter (D) to chamber height (H) is between about 3 and about 10.

* * * * *